United States Patent [19]

Blank

[11] Patent Number: 5,359,128

[45] Date of Patent: Oct. 25, 1994

[54] MALIC ACID DERIVATIVES AND COMPOSITIONS FOR THE TREATMENT OF PSORIASIS

[76] Inventor: Izhak Blank, 4 Simtat Arnon, Kiriat Ono, Israel, 55000

[21] Appl. No.: 16,778

[22] Filed: Feb. 11, 1993

Related U.S. Application Data

[63] Continuation of Ser. No. 643,553, Jan. 18, 1991, abandoned.

[51] Int. Cl.$^5$ .......................................... C07C 229/00
[52] U.S. Cl. .................. 560/169; 548/314.7; 548/496; 548/532; 548/339.1; 560/40; 560/147; 560/153; 560/168; 560/170; 560/180; 560/250; 560/251; 560/266; 562/445; 562/557; 562/560; 562/564; 562/567; 562/568; 562/582; 562/583
[58] Field of Search ................. 560/169, 170, 39, 250, 560/25, 169; 562/444, 448, 564, 567, 577; 568/413

[56] References Cited

U.S. PATENT DOCUMENTS

| | | | |
|---|---|---|---|
| 2,661,374 | 12/1953 | Schechter | 562/577 |
| 2,977,309 | 3/1961 | Godfrey . | |
| 3,212,970 | 10/1965 | Glasser . | |
| 3,778,502 | 12/1973 | Aubin . | |
| 3,983,100 | 9/1976 | Balme . | |
| 4,131,534 | 12/1978 | Just . | |
| 4,481,353 | 11/1984 | Nyilas et al. . | |

FOREIGN PATENT DOCUMENTS

| | | |
|---|---|---|
| 778342 | 2/1968 | Canada . |
| 0188749A2 | 7/1986 | European Pat. Off. . |
| 313446 | 4/1989 | European Pat. Off. . |
| 2530372A1 | 1/1977 | Fed. Rep. of Germany . |
| 2621214 | 11/1977 | Fed. Rep. of Germany . |
| 2621214C3 | 11/1977 | Fed. Rep. of Germany . |
| 2840498C2 | 4/1980 | Fed. Rep. of Germany . |
| 2840498 | 4/1980 | Fed. Rep. of Germany . |
| 2901452 | 7/1980 | Fed. Rep. of Germany . |
| 2901452C2 | 7/1980 | Fed. Rep. of Germany . |
| 3232883A1 | 3/1984 | Fed. Rep. of Germany . |
| 3812951 | 7/1989 | Fed. Rep. of Germany . |
| 1586682 | 2/1970 | France . |

WO89/1930  3/1989  PCT Int'l Appl. .
US/88/02941  10/1989  PCT Int'l Appl. .

OTHER PUBLICATIONS

W. Raab, H&G Nr. 10 (1984).
A. Lahti et al., Contact Dermatitis 12, 139–140 (1985).
Schafer G., Fumarsauretherapie der Psoriasis, Arztliche Praxis 30, 61, 1757–58 (1978).
Selecta 15, 1260–61 (1984).
Thaler et al., J. Invest. Dermatol. 75, 156–158 (1980).
Steinert et al., Biochemistry of Normal and Abnormal Differentiation, eds. I. A. Bereinstein and M. Seigji, Tokyo University Press, pp. 391–406 (1980).
J. March, Advanced Organic Chemistry, 3d ed., p. 339, J. Wiley and Sons, New York (1985).
Lochmueller, C. H. et al., Direct gas chromatographic resoltuion of enantiomers on optically active mesophases. IV. Effect of structure on selectivity and liquid crystalline behavior, J. Chromat. 178, 411–417 (1979).
Meek, J. L., Derivatizing reagents for high-performance liquid chromatography detection of peptides at the picomile level, J. Chromat. 266, 401–408 (1983).
Augustine, M., N-Maleyl amino acids and peptides, Z. Chem. 25, 18–19 (1985).
Portoghese, P. S. et al., Synthesis and opioid antagonist potencies of Naltrexamine Bivalent Ligands with Con- (List continued on next page.)

*Primary Examiner*—Michael L. Shippen
*Attorney, Agent, or Firm*—Curtis, Morris & Safford

[57] ABSTRACT

The invention comprises compositions and methods for the treatment of psoriasis. The compositions comprise compounds of the formula:

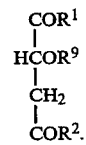

1 Claim, No Drawings

OTHER PUBLICATIONS formationally Restricted Spacers, J. Med. Chem. 29, 1650–1653 (1986).

Schellenberger, V. et al., A spectrophotometric assay for the characterization of the S' subsite specificity of α-chymotrypsin, Bioch. et Bioph. Acta 869, 54–60 (1986).

Nieboer, C. et al., Systemic therapy with fumaric acid derivatives: New possibilities in the treatment of psoriasis, J. Am. Acad. Derm. 20, 601–607 (1989).

Chemical Abstract No. 83-114855b (1975).

W. M. Nygteren-Hyying et al., Fourth International Symposium on The Treatment of Psoriasis and Psoriasis-Arthritis, Jerusalem, Israel, p. 60 (Mar. 1989).

G. Zubay, Biochemistry, 2nd Edtion, p. 334, Addison-Wesley Publishing Co. (Reading, Mass.) (1984).

C. Sreeramula Chetty et al., Arch. Int. Physiol. Biochem. 90(4), 293–6 (1982).

Gouesnard, Bull. Soc. Chim. Fr., 1, 88–94 (1989).

"Hackh's Chemical Dictionary" 4th Ed., p. 609 (1969).

S. E. Poet, Aust. J. Chem., 35, 77–83 (1982).

E. Wenkert, J. Org. Chem. 50, 4681–4685 (1985).

Chemical Abstract, vol. 100: No. 23, 191667p (1984).

Chemical Abstract, vol. 54: No. 7, 6698h–6699g (1960).

A. Lahti et al., Pharmaceutical Studies on Nonimmunologic Contact Urticaria in Guinea Pigs, Arch. Dermatol. Res., 299, 44–49 (1986).

Gouesnard, Bull. Soc. Chim. Fr, (1), pp. 88–94 (1989).

"Hackh's Chemical Dictionary," 4th Ed, p. 609 (1969).

Poet, Aust. J. Chem., 35, pp. 77–83 (1982).

Wenkert, J. Org. Chem., 50, pp. 4681–4685 (1985).

Bonadies, Chem. Abst., 100: 191667p (1984).

Muller, Chem. Abst. 54:6698h–6699g (1960).

MALIC ACID DERIVATIVES AND COMPOSITIONS FOR THE TREATMENT OF PSORIASIS

This application is a continuation of application Ser. No. 07/643,553, filed Jan. 18, 1991 now abandoned.

BACKGROUND OF THE INVENTION

Psoriasis is one of the most widespread chronic diseases. It affects about two percent of the adult white population, the most severe symptoms being shown by patients in the age groups between twenty and fifty years old.

Psoriasis is characterized by a greatly accelerated rate of epidermal turnover. Instead of the normal period of 28 days from the time of cell division in the basal layers until the cell is shed from the stratum corneum, in psoriasis this takes only about four days.

The causes and mechanism of development of psoriasis are unknown, and for this reason a completely effective treatment for this ailment does not yet exist. A great number of approaches have been tried, from the very old, based on natural tars, to the more modern using steroids, sporalene, etc. Tars are messy to apply and have only a limited effect. Their combination with sulfur and salicylic acid are not much better. This therapy is frequently supplemented by the use of ultraviolet (UV) radiation, either natural (sunshine) or artificial (lamps). Other compounds used are: steroids, azaribine, methotrexate, psoralen, and retinoic acid derivatives. All of these have a rather high toxicity and their long term use may result in noxious side effects.

A possible approach to the therapy of the disease is to try to influence cellular metabolism, which obviously is much more active in the psoriatic cells than in the normal ones.

A few years ago, a new treatment was proposed. This is based on the use of fumaric acid in the form of its simple mono- or diesters or its metal salts, based on the theory that in the psoriatic portions of the skin there exists an unbalance in the dicarboxylic-acids cycle conducive to lower levels of fumarate. This theory seems to be confirmed by the fact that some amino acids, such as glycine, are present in lower quantities in the psoriatic skin, compared to their content in normal skin. Since these amino acids are also derived from the dicarboxylic-acids cycle, their presence in lower quantities is an added corroboration to the above theory.

The treatment of psoriasis by fumaric esters and related compounds has been described with increasing interest. C. Nieboer et al., J. Am. Acad. Dermatol. 20, 601-8 (1989); W. M. Nygteren-Huying et al., Fourth International Symposium on the treatment of psoriasis and psoriasis-arthritis, Jerusalem, Israel (March 1989). There are at present thousands of patients being treated with tablets containing dimethyl fumarate as the main active ingredient. Although this treatment has shown some success, there are some serious questions about the side-effects caused by the prolonged use of the fumarate esters. The short term use of these compounds can also result in the occurrence of hot flashes, nausea and irritation of the gastrointestinal system.

A number of patent applications deal with the use of fumarate esters and salts for the treatment of psoriasis. GP 2530372 (13.1.77) describes the use of fumaric acid, fumarate esters, such as monoethyl and monomethyl fumarate, dimethyl fumarate, and some salts of the monoesters such as manganese, calcium, zinc, iron, etc. All of these can be mixed with other ingredients such as tartaric acid, citric acid, sugar, and inert fillers. Some of these formulations are for internal use and some for external (topical) application. Related applications, GP 2840498 (10.4.80) and GP 2901452 (17.7.80), describe the addition of glycine, 1-methionine, and 1-cysteine to the above mixtures of fumarate esters and salts. A recent European patent, 0188749 A2 (30.7.86) claims the use of fumarate esters of alcohols having one to eight carbon atoms, esters of higher alcohols (C6-C24), metal salts of the monoesters, and esters of diols, glycerol, and other hydroxyl-containing compounds. Another patent, GP DE 3232883 A1 mentions the preparation of salts of fumaric acid with various caffein-8-ethers. The salts are crystalline and can be used for the preparation of tablets, capsules, etc., in combination with metal salts of fumaric esters, as mentioned before, and also with the optional addition of amino acids such as cysteine and methionine, and of vitamin C.

There exist serious problems as to the use of the above in the therapy of psoriasis. Short-chain fumarate esters are in general irritating materials which frequently produce an unpleasant acidosis effect upon ingestion. Metal salts of the half esters are quickly converted in the stomach into the free acid and the respective metal hydrochloride. The same happens with the caffein-ether salt. The esters are liquid at room temperature and in order to convert them to tablets they have to be adsorbed on, or mixed with, a rather large quantity of inert carrier. Furthermore, they have a strong characteristic odor and their toxicology has not been studied extensively. According to a study made with mice, monoethyl fumarate and dimethyl fumarate given per os had an $LD_{50}$ above 100 mg/kg. Monoethyl fumarate, given intraperitoneally, was more toxic (W. Raab, H&G Nr. 10 (1984)). These fumarate esters are highly irritating to the skin and can produce contact urticaria (A. Lahti et al., Contact Dermatitis 12, 139-140 (1985)).

PCT International Application No. PCT/US88/02941 describes new derivatives of fumaric acid which, while retaining the effectiveness of fumarate, exhibit reduced side effects.

To summarize: mono and diesters of fumaric acid have been shown to be effective in the treatment of psoriasis, as the experience with several thousand patients indicates (see, for instance: Schafer G. Fumarsauretherapie der Psoriasis, Arztliche Praxis 30, 61 p. 1757-58 (1978); also, Selecta 15, p. 1260-61 (1984)). The esters are irritating to the digestive system and to the skin and their toxicology has not been clearly established; they are also difficult to formulate as tablets.

In biochemical terms the closest molecules to fumarate are maleate and malate.

Maleate is known to be ineffective in the treatment of psoriasis and is also more toxic than fumarate. On the other hand, malate and fumarate differ by hydrolysis of the unsaturated bond of fumarate. In the cell, fumarate is hydrated to malate by means of the enzyme fumarate hydratase (fumarase). The reaction is freely reversible with practically no energy barrier. G. Zubay, Biochemistry, 2nd Edition, p. 334, Addison-Wesley Publishing Co. (Reading, Mass.) (1984).

Studies in vitro have also shown the biochemical similarity between fumarate and malate. C. Sreeramula Chetty et al., Arch. Int. Physiol. Biochem. 90(4), p. 293-6 (1982). If psoriasis is related to a defect in the tricarboxylic acid cycle which can be compensated by the accumulation of fumarate, it is quite possible that malate could also have a similar effect. Moreover, malate also converts to oxaloacetate in the energy-generating tricarboxylic acid cycle, and it might be more effective in this respect.

Recent studies have shown that in psoriatic skin the content of glycine and serine is about twenty-five percent lower than in normal skin (Thaler et al., J. Invest. Dermatol. 75, 156–158 (1980); also, Steinert et al., Biochemistry of Normal and Abnormal Epidermal Differentiation, eds. I. A. Bereinstein and M. Seiji, Tokyo University Press, p. 391–406 (1980)). This deficiency may be related to the malate or fumarate imbalance or to other unknown causes. The addition of glycine as such, to such formulations, cannot contribute much to the therapeutic effect since this water-soluble material will be quickly incorporated into the general metabolic processes, so, at best, its value will be like an added food.

BRIEF DESCRIPTION OF THE INVENTION

Linking amino acids such as glycine, serine, etc., to malic acid via a chemical link such as via amide groups, results in conjugates which have a high efficacy in the treatment of psoriasis. The conjugate compounds are mostly stable crystalline solids. They are easy to formulate as tablets, ointments, or similar galenic forms. The amide bond is known to be more stable to hydrolysis than an ester group (see, for instance, J. March, Advanced Organic Chemistry 3rd ed. p. 339, J. Wiley & Sons, New York (1985)), and therefore the mal-amido amino acids convert at a much slower rate into the malate and the free amino acid. They easily absorb through the digestive system, since it is known that amides have good solubilization properties both with hydrophilic and lipophilic compounds.

In its broadest aspects, therefore, the invention relates to compositions and methods for delivering a residue of malic acid and one or more amino acids to humans. The compositions of the invention alleviate the symptoms of psoriasis. The compositions of the invention when administered per os also have the effect of stimulating digestion and appetite, and when administered per os or topically reduce the tanning effects of the sun.

The compounds of the invention are of formula $$\begin{array}{c} COR^1 \\ | \\ HCOR^9 \\ | \\ CH_2 \\ | \\ COR^2 \end{array}$$

or a pharmaceutically acceptable salt thereof, wherein:

$R^1$ and $R^2$ are the same or different and each is hydroxyl, lower alkyl, lower alkoxy, a residue of an amino acid of formula

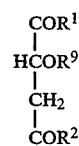

or

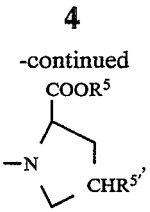

a peptide of formula

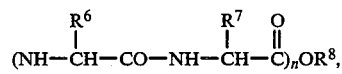

a peptide containing proline or hydroxyproline and one or more amino acids the same as or different than proline or hydroxyproline, alkylamino, alkarylamino, or arylamino;

$R^3$, $R^6$, and $R^7$ are the same or not all the same and each is a side chain of an amino acid;

$R^4$, $R^5$, and $R^8$ are the same or different and each is hydrogen or lower alkyl;

$R^{5'}$ is hydrogen or hydroxyl;

$R^9$ is hydrogen, lower alkyl or carbonyl $C_1$–$C_{25}$ alkyl; and n is an integer from 1 to 20; provided that:
(a) $R^1$ and $R^2$ are not both hydroxyl when $R^9$ is hydrogen; and
(b) $R^3$ is not

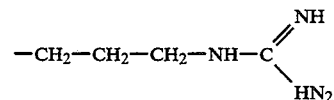

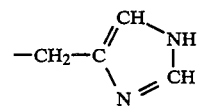

when one of $R^1$ and $R^2$ is hydroxyl and $R^9$ is hydrogen

DETAILED DESCRIPTION OF THE INVENTION

In an embodiment of the invention, the compounds of the invention include compounds of formula

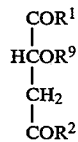

or a pharmaceutically acceptable salt thereof, wherein $R^1$ and $R^2$, which are the same or different, each designates (a)
(i) a residue of an amino acid or derivative thereof,
(ii) an ester of an amino acid or derivative thereof,
(iii) a salt of an amino acid or derivative thereof,
(iv) a peptide of two or more amino acids or derivative thereof, or
(v) an ester of said peptide or derivative thereof;

(b) a residue of an amino compound selected from the group consisting of lower alkylamines wherein the alkyl group contains up to 10 carbon atoms, alkarylamines, or arylamines, or (c) an OH group, provided that only one of said $R^1$ and $R^2$ may be OH when $R^9$ is hydrogen, and $R^9$ designates hydrogen, lower alkyl or carbonyl $C_1$-$C_{25}$ alkyl.

The term "amino acid" as used herein refers to the twenty alpha-amino acids commonly found in proteins, also called "standard amino acids," as well as certain rare amino acids found in fibrous proteins and some naturally occurring amino acids not found in proteins. With the exception of proline and hydroxyproline, all the alpha amino acids have a free carboxyl group and a free unsubstituted amino group on the alpha carbon atom. However, they differ from each other in the structure of their distinctive side chains, called the R groups, i.e., $R^3$, $R^6$, and $R^7$ above. The term "alkyl" refers to a straight or branched chain hydrocarbon radical containing no unsaturation and having 1 to 24 carbon atoms including, e.g., methyl, ethyl, propyl, isopropyl, 1-butyl, isobutyl, t-butyl, and the like. The term "lower alkyl" refers to an alkyl radical as defined above having 1 to 6 carbon atoms. The term "lower alkoxy" refers to an alkoxy radical having 1 to 6 carbon atoms The term "$C_1$-$C_{25}$ alkyl" refers to a straight or branched chain hydrocarbon radical having 1 to 25 carbon atoms. The term "alkyl amino" refers to an amino radical substituted by alkyl. The term "alkarylamino" refers to an amino radical substituted by an alkaryl radical. The term "arylamino" refers to an amino radical substituted by an aryl radical. The term "aryl" refers to an organic radical derived from an aromatic hydrocarbon by the removal of one hydrogen atom, such as, phenyl, tolyl, salicyl, naphthyl, etc. The term "alkaryl" refers to an aryl radical substituted by an alkyl radical.

In accordance with another embodiment of the invention, there are provided malate amido-amino acid compounds wherein the amino acids are selected from one or more of: alanine, glycine, serine, proline, valine, asparagine, glutamine, methionine, threonine, leucine, isoleucine, cysteine, cystine, phenylalanine, tyrosine, hydroxyproline, tryptophan, aspartic acid, glutamic acid, hydroxyglutamic acid, histidine, lysine, and arginine, as well as their derivatives, such as esters, salts, etc. Thus, for instance, it is possible to use in the formulations the malamide of ethyl glycinate or of sodium glycinate. In other words, it is possible to make use of the carboxylic acid group of the amino acid to further change the solubility and other characteristics of the compound.

Furthermore, since malic acid has two carboxyl groups, it is possible to prepare and make use of mixed amides, such as the glycine-serine-malamide. Accordingly, one skilled in the art will readily appreciate the large number of permutations using various combinations of amino acids and/or various combinations of peptides made up of various combinations of amino acids, as well as the esters of such compounds.

Advantageously, the compounds of the invention are mono-lauryl malamide, mono-serine malamide, serine-glycine-malamide, glycine-serine-malamide, di-serine-malamide, (serine-serine)- malamide, di-(serine-serine)-malamide, (glycine-glycine)-malamide, (serine-glycine)-malamide, di-(glycine-serine)-malamide, di-(serine-glycine)-malamide, (serine-glycine)-(glycine-serine)-malamide, a lower alkyl mono- or diester of any of said compounds, a lower alkyl mono- or diester of monoglycine malamide, a lower alkyl mono- or diester of di-glycine-malamide and a pharmaceutically acceptable salt of any of said compounds. It can be appreciated that the amide conjugates can be bonded at either or both carboxyl groups of malic acid.

The amino acid esters of the compounds are desirably lower alkyl esters containing from 1 to 4 carbon atoms in the alkyl group. Where $R^1$ or $R^2$ is an alkylamine, the alkyl group may contain broadly up to 24 carbon atoms, or, more narrowly, up to 10 carbon atoms. By using in the synthesis long-chain amines, it is possible to obtain malamides of particular interest for topical use. Suitable compounds are the amides of n-octylamine, 2-ethylhexyl amine, dodecylamine, octadecylamine, etc., in the form of simple and mixed diamides, or in combination with the amino acids and substituted amino acids as mentioned above. The introduction of long-chain amines into the molecule makes the resulting materials more lipophilic, and thus enhances the rate of transdermal penetration.

The compositions of the invention may contain the active compounds described above, as well as compounds wherein $R^1$ and $R^2$ are glycine and alkylamine containing up to 24 carbon atoms, together with a pharmaceutically acceptable carrier as is known in the art. The carriers may include vehicles for immediate or sustained release and may be in a variety of dosage forms as are also known in the art.

The methods of the invention include, broadly, a method for delivering residues of malic acid and/or amino acids to a patient by administering the compositions of the invention, either per os or topically, as circumstances dictate. The compositions of the invention may be used to alleviate the symptoms of psoriasis. They may also be used to stimulate the appetite, and to reduce the tanning effects of the sun.

Each psoriasis patient represents a unique clinical and therapeutic picture. There is no set or recommended dose for the treatment of psoriasis using the compositions of the invention. In order to determine the correct dose for the treatment of psoriasis, the physician must follow a simple program of escalating dosage until either a beneficial response is attained or untoward side effects intervene.

It is well known to the art to administer compositions containing fumaric acid derivatives for the treatment of psoriasis in gradually escalating dose until clinical improvement is manifested. The dose is increased over a period of weeks until such clinical improvement is attained. In this event the dose is maintained at the level which provides the optimum benefit. If no benefit is realized, the dose is increased unless untoward side effects intervene. This procedure is followed for the treatment of psoriases by means of fumaric acid, Fumarderm P ™ (a tablet compounded of dimethylester fumarate, 120 mg; monoethylester-Ca, 87 mg; monoethylester-Mg, 5 mg; monoethylester-Zn, 3 mg), and for treatment of psoriasis by diglycylfumaramide diethyl ester. Thus, one skilled in the art would know to commence treatment with a relatively low dose of the composition of the invention, such as approximately 750 mg taken in separate doses twice a day, and increase the dose as needed until either clinical resolution or side effects become apparent. A homologous compound, diglycylfumaramide of diethyl ester has been determined to possess very low toxicity in comparison to fumaric acid or fumarate esters.

Thus, in accordance with another embodiment of the invention, there is provided a pharmaceutical composition for alleviating the symptoms of psoriasis and other skin diseases which comprises an amount effective for alleviating the symptoms of psoriasis and other skin diseases of a compound of formula $$\begin{array}{c} COR^1 \\ | \\ HCOR^9 \\ | \\ CH_2 \\ | \\ COR^2 \end{array}$$

or a pharmaceutically acceptable salt thereof, wherein:

$R^1$ and $R^2$ are the same or different and each is hydroxyl, lower alkyl, lower alkoxy, a residue of an amino acid of formula

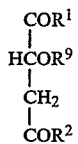

$$-NH-CH(R^3)-COOR^4$$

or

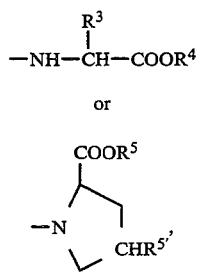

a peptide of formula

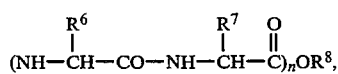

$$(NH-CH(R^6)-CO-NH-CH(R^7)-C(O))_n OR^8,$$

a peptide containing proline or hydroxyproline and one or more amino acids the same as or different than proline or hydroxyproline, alkylamino, alkarylamino, or arylamino;

$R^3$, $R^6$, and $R^7$ are the same or not all the same and each is a side chain of an amino acid;

$R^4$, $R^5$, and $R^8$ are the same or different and each is hydrogen or lower alkyl;

$R^{5'}$ is hydrogen or hydroxyl;

$R^9$ is hydrogen, lower alkyl or carbonyl $C_1$–$C_{25}$ alkyl; and n is an integer from 1 to 20.

In addition, there is provided a pharmaceutical composition for stimulating digestion or appetite, or reducing the tanning effect of exposure to the sun which comprises an amount effective for reducing the tanning effect of exposure to the sun of a compound of formula $$\begin{array}{c} COR^1 \\ | \\ HCOR^9 \\ | \\ CH_2 \\ | \\ COR^2 \end{array}$$

or a pharmaceutically acceptable salt thereof, wherein:

$R^1$ and $R^2$ are the same or different and each is hydroxyl, lower alkyl, lower alkoxy, a residue of an amino acid of formula $$-NH-CH(R^3)-COOR^4$$

or

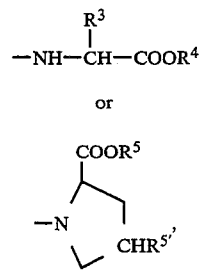

a peptide of formula

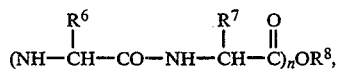

$$(NH-CH(R^6)-CO-NH-CH(R^7)-C(O))_n OR^8,$$

a peptide containing proline or hydroxyproline and one or more amino acids the same as or different than proline or hydroxyproline, alkylamino, alkarylamino, or arylamino;

$R^3$, $R^6$, and $R^7$ are the same or not all the same and each is a side chain of an amino acid;

$R^4$, $R^5$, and $R^8$ are the same or different and each is hydrogen or lower alkyl;

$R^{5'}$ is hydrogen or hydroxyl;

$R^9$ is hydrogen, lower alkyl or carbonyl $C_1$–$C_{25}$ alkyl; and n is an integer from 1 to 20.

The materials of this invention are nonirritating to the skin. The amide conjugates are mild and nonirritating. Glycine is used in some formulations of aspirin tablets with the object of reducing gastric irritation. Any amount of glycine produced in the stomach by hydrolysis of the amide, will actually act in a beneficial way, in this respect.

Malic acid has two forms, D and L. Malic acid derivatives derived from the D-form, the L-form, or mixtures of the D- and L-forms are encompassed within the scope of the present invention.

The invention is illustrated by the following examples which are not limiting.

EXAMPLES

EXAMPLE 1

Acetate of the Malic Diamide of Glycine ethyl ester (GMAE)

Three equivalents of acetyl chloride were added dropwise in a flask to one equivalent of malic acid while keeping the temperature below 0° C. After the acetyl chloride was added, the mixture was stirred at room temperature overnight. Excess acetyl chloride and acetic acid were then distilled under a water pump at room temperature to provide malic anhydride acetate.

Five grams of the anhydride obtained above were dissolved in 20 ml chloroform, one equivalent of water was added and the mixture was stirred at room temperature overnight. The solvent was distilled at reduced pressure keeping the temperature below 40° C. providing malic acid acetate as a white solid (melting point 132° C.).

Three equivalents of thionyl chloride were added dropwise in a flask to one equivalent of the malic acid acetate keeping the temperature at 0° C. The mixture was stirred overnight. The liquid phase became homogeneous. Excess thionyl chloride was removed by vacuum. The resulting product dichloride of malic acid acetate was an oil which crystallized upon standing.

A saturated sodium bicarbonate solution (five equivalents) was cooled to less than −5° C. Two equivalents of glycine ethyl ester hydrochloride were added and the solution was stirred. Separately, a solution of one equivalent of the dichloride of malic acid acetate in acetone was prepared and added dropwise to the glycine ethyl ester hydrochloride solution. After the addition was completed, the solution was stirred for thirty minutes.

The precipitate was filtered, washed and dried at 40° C. to provide GMAE as a white powder. GMAE is insoluble in water, soluble in chloroform, and has a melting point of 138°–139° C.

C(calc) 48.7%; found: 48.3%, 47.9%. N(calc) 8.1%; found:
8.0, 8.0%. H(calc) 6.1%; found 6.4%, 6.8%.

The material was further characterized by NMR.

The final product GMAE is the acetate of the diamide. Blocking of the hydroxyl group of malic acid increases the lipophilicity of the molecule. In the body this acetate is hydrolyzed back to the free hydroxyamide.

EXAMPLE 2

Acetate of Lauryl malamide (LMA)

The procedure is similar to the one described in Example 1 except lauryl (dodecyl) amine hydrochloride is used in place of glycine ethyl ester hydrochloride.

EXAMPLE 3

Acetate of Serine malamide (SMA)

The procedure is similar to the one described in Example 1 except serine hydrochloride is used in place of glycine ethyl ester hydrochloride.

EXAMPLE 4

Acetate of Glycyl-lauryl malamide (GLMA)

The procedure is similar to the one described in Example 1 except lauryl (dodecyl) amine hydrochloride and glycine hydrochloride are used in place of glycine ethyl ester hydrochloride.

EXAMPLE 5

Acetate of Methyl ester of diglycyl malamide (MGMA)

The procedure is similar to the one described in Example 1 except glycine methyl ester hydrochloride is used in place of glycine ethyl ester hydrochloride.

GALENIC FORMS

EXAMPLE 6

Capsules

Pure GMAE prepared as per Example 1 is put in gelatin capsules (100 mg. each) and these are given to patients suffering from psoriasis, at a rate effective to reduce the patient's lesions.

EXAMPLE 7

Tablets

The same material is granulated with 1% polyvinylpyrrolidinone and 0.2% magnesium stearate and then is compressed into tablets. These are hard and nonfriable.

EXAMPLE 8

Gel 40 parts by weight GMAE, 30 parts by weight propylene glycol, 4 parts by weight isopropyl myristate, 6 parts by weight cetyl alcohol, and 22 parts by weight ethanol are mixed well. The resulting gel is packed in tubes and advantageously is used for the topical treatment of psoriasis patients.

The same material also advantageously is used for the treatment of a patient with a localized hyperkeratosis.

EXAMPLE 9

Gel

LMA prepared as per Example 2, 38.4 parts by weight are mixed with 12.1 by weight cetyl alcohol, 11.4 parts by weight isopropyl myristate, 11.6 parts by weight propylene glycol, 20.1 parts by weight ethanol, and 1.4 parts by weight silica. The resulting gel is packed in tubes and is used for the topical treatment of psoriatic wounds.

EXAMPLE 10

Gel

A gel is prepared as described in Example 9 but using the material of Example 4 (GLMA).

EXAMPLE 11

Shampoo

The material of Example 4 (GLMA) has surfactant properties and is a medium foamer. When diluted with water to a 10% concentration it is used as a scalp wash for alleviating psoriatic wounds in that area of the body. At a dilution of 5% it is used as a bath shampoo.

I claim:

1. A compound of formula

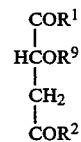

or a pharmaceutically acceptable salt thereof, wherein:
$R^1$ and $R^2$ are the same and each is a residue of an amino acid of formula

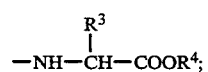

$R^3$ is H;
$R^4$ is ethyl; and
$R^9$ is

* * * * *